(12) United States Patent
Xie et al.

(10) Patent No.: US 10,076,527 B2
(45) Date of Patent: Sep. 18, 2018

(54) STANDARDIZED EXTRACT AND ITS USE IN THE MANUFACTURE OF A MEDICAMENT

(71) Applicant: BOTANIC CENTURY (BEIJING) CO., LTD., Beijing (CN)

(72) Inventors: Chen Xie, Beijing (CN); Xiuzhen Luo, Beijing (CN); Yun Qi, Beijing (CN)

(73) Assignee: Botanic Century (Beijing) Co., Ltd., Beijing (CN)

( * ) Notice: Subject to any disclaimer, the term of this patent is extended or adjusted under 35 U.S.C. 154(b) by 373 days.

(21) Appl. No.: 14/735,410

(22) Filed: Jun. 10, 2015

(65) Prior Publication Data

US 2015/0335661 A1 Nov. 26, 2015

Related U.S. Application Data

(62) Division of application No. 12/373,235, filed as application No. PCT/CN2007/002108 on Jul. 9, 2007, now Pat. No. 9,056,046.

(30) Foreign Application Priority Data

Jul. 10, 2006 (CN) .......................... 2006 1 0098564

(51) Int. Cl.
| | |
|---|---|
| *A61K 36/42* | (2006.01) |
| *A61K 36/185* | (2006.01) |
| *A61K 31/575* | (2006.01) |
| *A61K 9/00* | (2006.01) |
| *A61K 9/02* | (2006.01) |
| *A61K 31/57* | (2006.01) |

(52) U.S. Cl.
CPC .......... *A61K 31/575* (2013.01); *A61K 9/0031* (2013.01); *A61K 9/02* (2013.01); *A61K 31/57* (2013.01); *A61K 36/42* (2013.01)

(58) Field of Classification Search
None
See application file for complete search history.

(56) References Cited

U.S. PATENT DOCUMENTS

2003/0203052 A1* 10/2003 Dreyer ..................... A61K 8/11
424/725
2005/0025737 A1 2/2005 Sebagh

FOREIGN PATENT DOCUMENTS

| CN | 86106088 A | 3/1988 |
| CN | 1520856 A | 8/2004 |
| JP | 57077610 A | 5/1982 |

OTHER PUBLICATIONS

The Ministry of Health, China, Cucurbitacins Tablet, Standard Specification of Traditional Chinese Medicines, 1988, vol. 19m, pp. 223-224.
Cheryl Charming, the book of the Everything Cocktail Parties and Drinks Book; the Ultimate Guide to, p. 288, 2005.
Xiong et al., Separation of Cucurbitacins B and Cuburbitacins E from Fruit Base of *Cucumis melo* L. by High-Speed Countercurrent Chromatography, ACS Symposium Series, American Chemcial Society, Washington DC, 1985 pp. 107-110.

* cited by examiner

*Primary Examiner* — Chris R Tate
*Assistant Examiner* — Randall Winston
(74) *Attorney, Agent, or Firm* — Dickinson Wright, PLLC

(57) ABSTRACT

The present invention refers to a medicament which activates gastrointestinal movement. The medicament consists essentially of Cucurbitacin D and one or more substances form the group including Cucurbitacin A, Cucurbitacin B, Cucurbitacin E, Isocucurbitacin B and Isocucurbitacin D. The medicament is made from an extract obtained from Muskmelon Base, the fruit stem of *Cucumis melo* L. The medicament can promote enterokinesia in both normal animals and in animal models where gastrointestinal movement is inhibited. It has also been demonstrated to activate the movements of the stomach, small and large intestines. The extract may be used alone or in combination with the other botanical ingredients or chemical substances to form the pharmaceutical preparation.

26 Claims, 12 Drawing Sheets

STANDARDIZED EXTRACT AND ITS USE IN THE MANUFACTURE OF A MEDICAMENT

RELATED APPLICATIONS

Figure 1A:
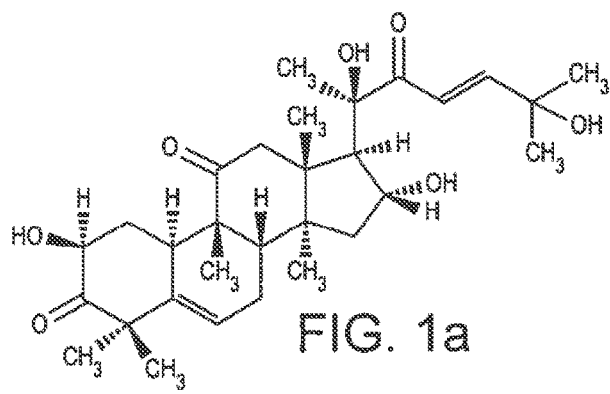

This application is a divisional of U.S. application Ser. No. 12/373,235, filed Jan. 9, 2009, which is the National Stage of International Application No. PCT/CN2007/002108 filed Jul. 9, 2007, which claims the benefit of Chinese Application No. 200610098564.9 filed Jul. 10, 2006.

TECHNICAL FIELD OF THE INVENTION

The present invention relates a standardized extract, a pharmaceutical formulation and the extracts use in the manufacture of a medicament for treating a number of different conditions.

BACKGROUND OF THE INVENTION

After abdominal surgery, normal intestinal movement function may not routinely recover in 24 hours due to both trauma and anesthesia (causing early-stage postoperative enteroparalysis or ileus). The intestinal function will be affected by one or more of: irritation, effusion of abdominal cavity, inflammation and anesthesia effect, which cause intestinal distension and synechia. The later is the main cause of ileus.

It has been reported that the incidence rate of intestinal synechia is as high as 60-70% in all abdominal surgery, 5% of which develop intestinal ileus. The recurrence rate of ileus is high (over 15%) after synechia lysis. Indeed, the more operations, the higher the recurrence rate. [Editor: Chen Qi, Thoughts and Methods in Study on Medicinal Effectiveness of Chinese Medicine, People's Medical Publishing House p. 491-492, 2005].

The current treatments for intestinal distension and synechia in the clinic are Neostigmine injection or oral-administration of different "purgative" TCM formulas.

Although Neostigmine injection has good effect, and there are no restraints on its use, it has been reported that it could cause significant side effects, e.g. intestinal colic, increased gland secretion and muscle vibration. [Jiang M X and Yang Z C: Medical Pharmacology, People's Medical Publishing House, 3rd ed. Beijing, 1997, p 116].

The alternative, oral-administration of TCM formulas, also has some disadvantages, e.g. large volumes are difficult to take, and are not traditionally recommended immediately post operatively (postoperative patients should be fasted until flatus occurs and flatus is a sign of recovering gastrointestinal function). It has however been reported that the earlier the use of TCM formula after surgery, the better the therapeutic results could be. [Ma G X and Hou B Z: Clinical analysis on 405 cases of postoperative intestinal distension with Pai Qi Decoction, Chinese Medicine of Factory and Mine, 2002, 15 (1): p 72-73].

Kudingxiang (Muskmelon-Base) is the dried fruit stem of *Cucumis melo L.* (Cucurbitaceae family). The functions and indications of Muskmelon-Base (Kudingxiang) described in the Chinese Materia Medica (Vol. V. pp. 4580) and Inner Mongolia Standard for Materia Medica (1988, pp. 64) are:
Inducing vomiting and diuresis,
Expelling dampness and reducing jaundice.
It is used to treat:
Stroke,
Epilepsy,
Sore throat,
Phlegmatic hygrosis choking,
Shortness of breath,
Dyspepsia,
Abdominal fullness, and
Damp-heat type of jaundice in TCM terms.

It is regarded as an emetic herb in the TCM system due to its stimulating action upon the gastric mucosa and its reflex triggering of the central vomiting nerve.

Cucurbitacins are the main chemical substances in Muskmelon Base. It has been reported in the journal of Chinese Traditional and Herbal Drugs (Vol. 23, No. 11, 1992) that Cucurbitacins have cytotoxicity and anti-tumour activity, offer hepatic protection, anti-hepatitis, improvement of immune function, anti-chemocarcinogenesis, an increase of capillary permeability, and induced vomiting.

A product made from Muskmelon Base, and currently sold in the Chinese markets, is "Hu Lu Su" tablet (meaning Cucurbitacins tablet). The product specification was recorded in the 'Standard Specification of Traditional Chinese Medicines (Vol. 19)' issued by the Ministry of Health, China.

The tablets comprise a purified ethanol extract of the raw material of Muskmelon Base and the main chemical in the tablet is Cucurbitacin B, the content of which is no less than 60% as stated in the above Standard Specification. The functions and indications for the tablet include:
Eliminating toxins and clearing heat, and
Inducing diuresis and expelling jaundice
and it is used as an adjunct treatment for persistent hepatitis due to severe toxic heat, chronic hepatitis and primary hepatic carcinoma.

Muskmelon Base did not have the function of 'purgation' in TCM but Edery et al. reported that intravenous injection of Cucurbitacin D isolated from *Ecballium elaterium L.* induced diarrhea in conscious cats and dogs, and also stimulated enterokinesia in anesthetized dogs. But on the isolated guinea pig ileum, a concentration of 54 mg/ml Cucurbitacin D did not cause any visible effect. [H. Edery, G. Schatzberg Porath, S. Gitter, Pharmacodynamic activity of Elatericin (Cucurbitacin D) Arch Int Pharmacodyn. 1961, 13 (3~4):315~335].

It is an aim of the present invention to develop a medicament which will prevent intestinal distension and synechia and speed up gastroenterokinesia restoration. Such a medicament will have a significant impact on a patient's recovery after surgery.

The applicant has developed a standardized extract comprising Cucurbitacin D from *Cucumis melo L* and used this to develop a formulation for rectal delivery which has proved effective in animal studies.

The extract may be used alone or in combination with the other botanical ingredients or chemical substances to form the pharmaceutical preparation.

Furthermore the formulation avoids the hepatic by-pass effect associated with oral forms, is quick acting and would appear to benefit from no obvious muscle spasm side effect, a problem with Neostigmine the current preferred treatment.

TECHNICAL FIELD OF THE INVENTION

According to a first aspect of the present invention there is provided a standardized extract of *Cucumis melo L.*

The extract is standardized by reference to the content of one or more members of the family of compounds known as Cucurbitacins (including the Isocucurbitacins).

These include Cucurbitacin D, Cucurbitacin A, Cucurbitacin B, Cucurbitacin E, Isocucurbitacin B and Isocucurbitacin D.

Preferably the extract is standardized with reference to Cucurbitacin D which is believed to be an active ingredient.

However, the extract may alternatively be standardized with reference to Cucurbitacin B.

Indeed, the extract may be standardized by reference to an amount/range of both Cucurbitacin D and Cucurbitacin B.

Preferably the extract is a whole extract of Cucurbitacins.

Alternatively, the extract may be a purified or a selective fraction.

The extract or a selective fraction preferably comprises at least Cucurbitacin D and more preferably additionally Cucurbitacin B.

Indeed, it could comprise, without limitation, any permutation of the two, three, four, five or six specified Cucurbitacins and Isocucurbitacins.

Most preferably the extract comprises the Cucurbitacins B and D plus at least one of the following: Cucurbitacin A, Cucurbitacin E, Isocucurbitacin B and Isocucurbitacin D.

Even more preferably the extract comprises the Cucurbitacins B and D together with each of the following: Cucurbitacin A, Cucurbitacin E, and optionally also, each of Isocucurbitacin B and/or Isocucurbitacin D.

It will be apparent from the above that in order to arrive at a consistent extract it is important to standardize the dose against one or more markers/perceived actives.

In a favored embodiment the ratio of Curcurbitacin B/Curcurbitacin D in the extract is from between 30:1 to 1:10, more preferably still between 10:1 and 1:2 and most preferably still between 3:1 and 1.1.

Since the applicant has demonstrated that extracts containing both Cucurbitacin D and Cucurbitacin B demonstrate activity, it is preferred that one or more of these compounds are used to standardize the extract for use as a medicament. Indeed standardizing the extract against Cucurbitacin D or B content or within a closely defined range may be preferred.

Extracts according to the invention can be obtained by a number of alternative extraction methodologies which may additionally include further "purification" or additional extraction steps.

By way of example only, suitable solvent extraction methods include, but are not limited to, the use of water, polar solvents, such as ethanol and methanol, and their aqueous solutions.

The extraction methods, using the solvents mentioned above, include heat reflux extraction (including soxhlet extraction), percolation and maceration at room temperature.

The preferred solvent is water.

The preferred extraction method is a heat reflux extraction.

Based on the physical property of the raw material and the quantity of water used, the extraction process may be repeated up to four times. The usual extraction duration is 0.5-2 hours and the preferred extraction duration is one hour. The water quantity to be used is 8-10 folds of the raw material weight.

Preferably, the extraction is followed by a purification step. The preferred purification step is an ethanol precipitation step.

When the first concentrate is added to the ethanol solution the final ethanol concentration should be between 50% and 80%, preferably 70%. Under this condition, the content of the active compounds and composition are most suitable for the pharmaceutical application.

Thus, a preferred combined extraction and purification process may comprise the steps of:
  Pulverizing the raw material of Muskmelon Base,
  Extracting with water and obtaining a liquid extract,
  Concentrating the liquid extract to obtain a first concentrate,
  Adding the first concentrate to ethanol,
  Stir thoroughly, set aside, filter and concentrate the solution to obtain a second concentrate,
  Recover the ethanol and dry the second concentrate to obtain a purified extract.

Alternative or additional purification processes include liquid-liquid purification and resin purification.

Thus, the first and second concentrates of, for example, the preferred combined extraction purification process outlined above may additionally be purified by liquid-liquid partition. Suitable solvents include chloroform, methylene chloride, ether, and ethyl acetate.

A liquid-liquid partition step should usually be carried out a plurality of times, say 2-5 times, preferably 3 times.

After the liquid-liquid partition, the solvents are recovered. The concentrates from the liquid-liquid partition are dried to obtain extracts which can be used in the manufacture of a medicament.

An alternative purification method is to dissolve the first or second concentrates in water, and place the solution onto a column filled with a macro-porous resin. The process may comprise the steps of:
  Wash the column with water,
  Allow it to run through the column,
  Throw the water solution,
  Elute with one, or several, of the following solvents: methanol, ethanol, aqueous ethanol and aqueous methanol,
  Collect the eluents,
  Concentrate the eluent under vacuum and recover the solvent, and
  Dry the concentrates to obtain a purified extract.

The macro-porous absorption resin can be D 101, AB-8 or any other suitable resin.

D-101 is manufactured by Huishi Resin Factory, Shanghai, China. It is a non-polar resin with the following specification:

TABLE 1

| % Water | 65-75 |
| Wet density g/ml | 0.65-0.75 |
| Particle size (0.25-0.84 mm) | > or = to 95 |
| Surface area rate $m^2g$ | 500-550 |
| Average chamber diameter | 90-100 |

AB-8 is manufactured by Nankai Chemicals, Tianjin, China. It is a non-polar resin with the following specification:

TABLE 2

| % Water | 65-75 |
| Wet density g/ml | 1.00-1.10 |
| Particle size (0.25-0.84 mm) | > or = to 95 |
| Surface area rate $m^2g$ | 480-5250 |
| Average chamber diameter | 13-14 |

The elution can be an isocratic or gradient elution.

The drying methods used in the preparation of the extracts may include, but are not limited to, vacuum drying, and spray drying.

According to a second aspect of the present invention there is provided a pharmaceutical formulation comprising a standardized extract of *Cucumis melo L* in unit dosage form.

Preferably the pharmaceutical formulation is standardized with reference to a Curcurbitacin (including isocurcurbitacins).

Most preferably the standardizing Curcurbitacin is Curcurbitacin D, although Curcurbitacin B may be used.

Preferably, where the ratio of Cucurbitacin B/Cucurbitacin D is between 3:1 and 1:1, the formulation is standardized to provide a daily dose (based on a 65 kg patient) containing from 0.0040 mg to 40 mg of Cucurbitacin D, more preferably from 0.04 mg to 4.0 mg of Cucurbitacin D and most preferably still between 0.1 mg and 1.6 mg, with the preferred standard dose containing about 0.40 mg.

Alternatively, where the ratio of Cucurbitacin B/Cucurbitacin D is between 3:1 and 1:1, the formulation may be standardized to provide a daily dose (based on a 65 g patient) containing from 0.0064 to 64 mg Cucurbitacin B, more preferably from 0.064 to 6.4 mg Cucurbitacin B and most preferably still between 0.16 mg and 2.6 mg, with the preferred standard dose containing about 0.64 mg.

Preferably the pharmaceutical formulation is suitable for rectal delivery. Most preferably it takes the form of a suppository.

The carriers for rectal administration include:

Lipopholic bases including: natural fatty acid esters, semi-synthetic glycerides or hydrogenated vegetable oil;

Hydropholic bases including: gelatin glycerin, polyethylene glycol, polyoxyl [40] Stearate, Tween 61, polyoxyethylene sorbitan monostearate or poloxamer (Pluronics);

Additives including: surfactants such as Tween 80;

Chelators including: EDTA, trisodium citrate dehydrate or enamine derivatives;

Nonsteroidal anti-inflammatory agents including: sodium salicylate;

Antioxidants including: Butylated hydroxyanisole (BHA), Butylated hydroxytoluene (BHT) or Gallocatechin gallate; and Preservatives including para-hydroxybenzoic acid esters.

The medicament administrated by a rectal route is absorbed through the rectal mucosa and consequently about 50% to 70% of the medication does not go into the liver. As a result metabolism of the medication in the liver, and liver toxicity, are reduced. The rectal administration also avoids irritation to the gastric mucosa.

A rectal suppository is easy to use and it can be given to in-patients as well as out-patients. It is easily absorbed, fast to take effect and has high bioavailability. The medicament can shorten the duration of the recovery and rehabilitation post operatively with no limitation on the subject's gastrointestinal function.

However, alternative modes of delivery are contemplated and within the scope of the invention.

Thus, the extracts can be made into different dosage forms by conventional pharmaceutical preparation. The extract of the invention may be combined with any physiological acceptable drug carrier to form a pharmaceutical preparation in order to provide the medication to the subjects through different routes, for example, oral or via injection. Injectable forms include subcutaneous injection, intradermal injection, intramuscular injection, intraperitoneal injection, intravenous injection, intranasal injection and acupoint injection. Alternatively the medicament might be introduced directly at the surgical site.

The extract in the present invention could be made into injectable medications including solutions, emulsions, suspensions and injectable powders. As injection formulations, physiological acceptable carriers include pharmaceutically acceptable medium and additives may be used. The pharmaceutically acceptable mediums include water, non-aqueous solvents, or compound solvents. The non-aqueous solvents include injectable oils, ethanol, glycerin, propylene glycol, polyethylene glycol, benzyl benzoate, dimethyl acetamide, dimethyl sulfoxide, and isopropyl myristate. The additives include solubilizers, antioxidants, isotonic regulator, buffer, suspending agents, stabilizers, chelating agent, antibacterial agent, and filler, such as Tween-80, phosphate, methyl cellulose, creatinine, sodium sulfite, sodium choiride, ethylene diamine tetra-acetic acid disodium salt, lactose, and phenol.

Based on significant pharmacological studies, the applicant has found that a Muskmelon-Base extract made from, for example, aqueous extraction and ethanol precipitation possesses significant beneficial effects including the following:

Activating gastroenterokinesia;
Stimulating gastrointestinal movement in non-surgery
Impelling the large and small intestines;
Activating gastric emptying; and
Shortening the excretion intervals and increasing the quantity of faeces.

According to a third aspect of the present invention there is provided a standardized extract of *Cucumis melo L* for use in the manufacture of a medicament for the treatment of, or to effect, one or more of the following conditions:

Activating gastroenterokinesia;
Postoperative gastroenterokinesia restoration;
Shortening the duration of postoperative flatus;
Treatments of constipation;
Treating postoperative intestinal adhesion;
Treating Intestinal adhesion and ileus;
Stimulating gastrointestinal movement in non-surgery;
Impelling the large and small intestines;
Activating gastric emptying;
Smoothes bowel movement; and
Shortening excretion intervals and increasing the quantity of faeces.

It will be apparent from the above that in order to arrive at a consistent extract it is important to standardize the dose against one or more markers/ perceived actives.

Since the applicant has demonstrated that extracts containing both Cucurbitacin D and B demonstrate activity, it is preferred that one or more of these compounds are used to standardize the extract for use as a medicament.

The preferred marker is Curcurbitacin D although Curcurbitacin B or another Cucurbitacin or Isocucurbitacin may be used.

In a favored embodiment the ratio of Curcurbitacin B/Curcurbitacin D in the extract is from between 30:1 to 1:10, more preferably still between 10:1 and 1:2 and most preferably still between 3:1 and 1.1.

Preferably the amount of Curcubitacin D present in the total weight of Curcubitacins, including isocurcubitacins, comprises from 5% to 50%, more preferably 8% to 41%.

More particularly, the applicant has demonstrated that:

1. After a single dose rectal administration of the medicament, the proximal colon constriction of anaesthetised rats was significantly improved within 30 minutes, and it reached a peak between 30 min. and 60 min.
2. The medicament of the present invention can significantly activate the intestinal impellent of the mice with intestinal mechanical injury. At a high dose its function was equivalent to Neostigmine, but was without muscle spasm, a common side effect found with Neostigmine.

3. The medicament can additionally:
   Activate the intestinal impellent of the animals with gastrointestinal hypo-function induced by atropine,
   Shorten the excretion intervals,
   Increase the quantity of faeces, (count for 4 hours) and
   Improve the function of gastric emptying in the animals with gastrointestinal hypo-function induced by atropine.

As stated above, the medicament of the present invention can promote gastroenterokinesia in both normal and inhibited gastrointestinal animals and also promote movements in the stomach, small and large intestines. Comparatively speaking the strength of the effect is in order: large intestine>small intestine>stomach.

The Muskmelon-Base extract possesses the excellent features of:
   A small dosage quantity,
   A low frequency of administration (potentially single dose), and
   A fast onset of action.

Practically, the Muskmelon Base extract can activate gastroenterokinesia, and based on its characteristics, can be used in the treatment or prevention of:
   Constipation,
   Intestinal adhesion and ileus, and
   Promotion of flatus in order to activate gastroenterokinesia restoration after abdominal surgery.

According to a forth aspect of the invention there is provided a method of treatment of the human or animal body comprising administering an extract or pharmaceutical formulation of the invention to a patient.

Figure 1B:
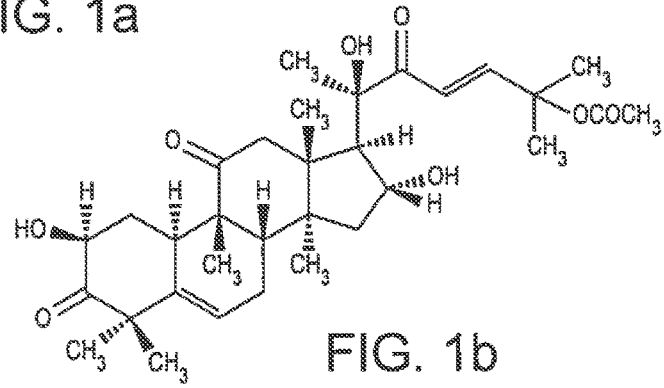
Figure 1C:
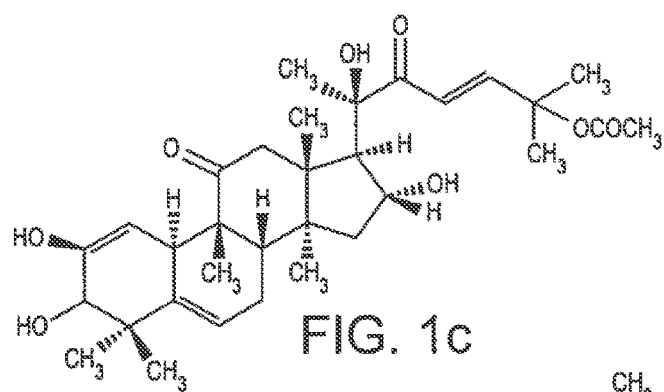
Figure 1D:
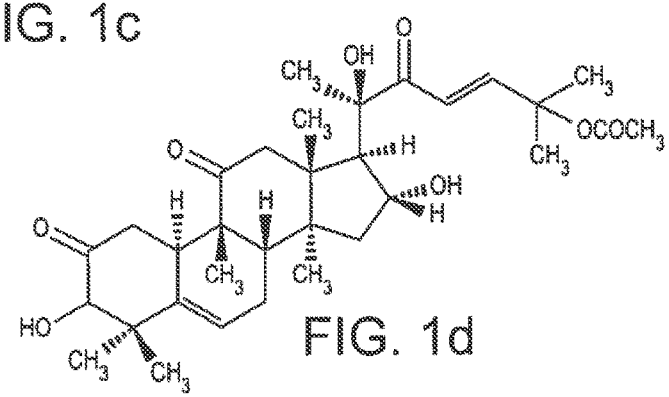
Figure 1E:
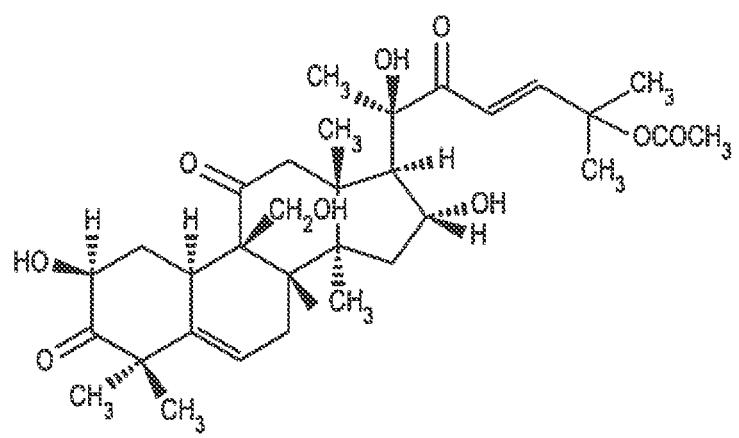
Figure 1F:
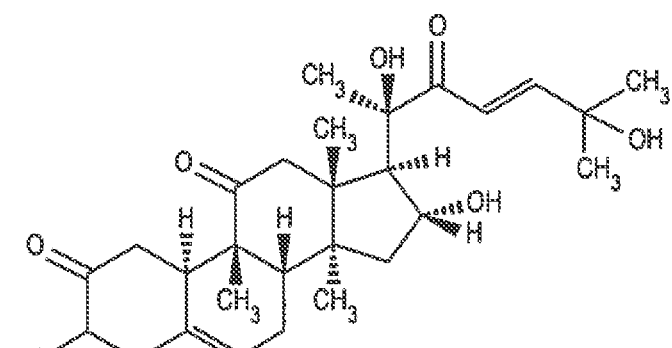
Figure 2A:
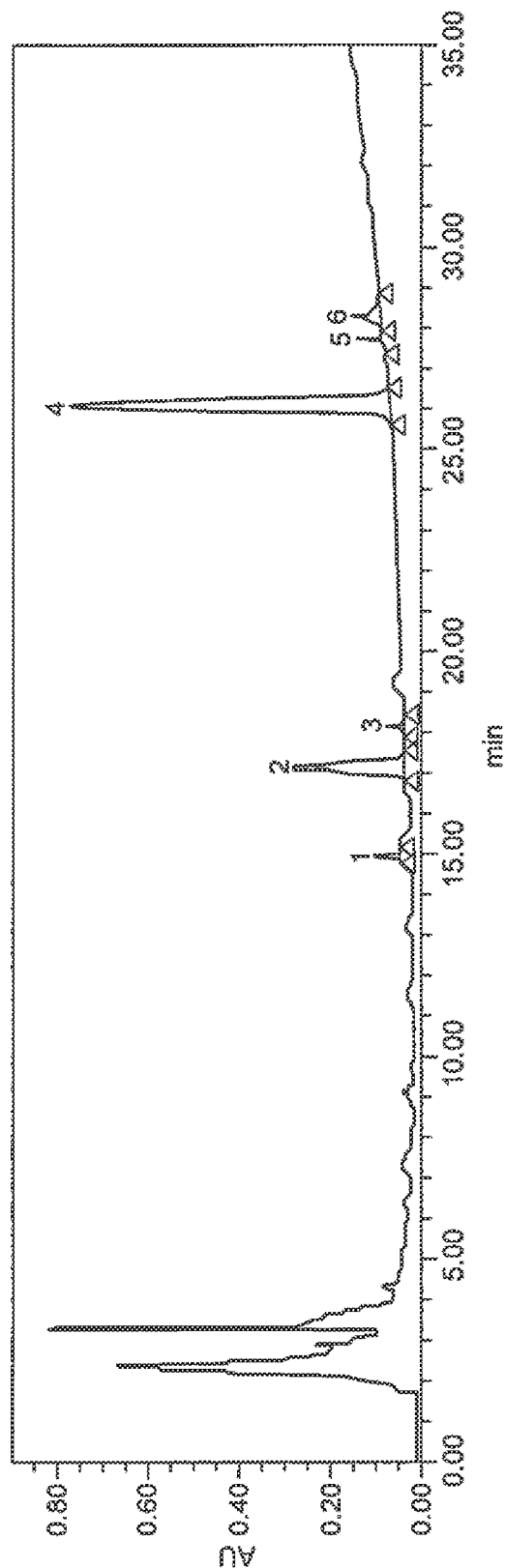
Figure 2B:
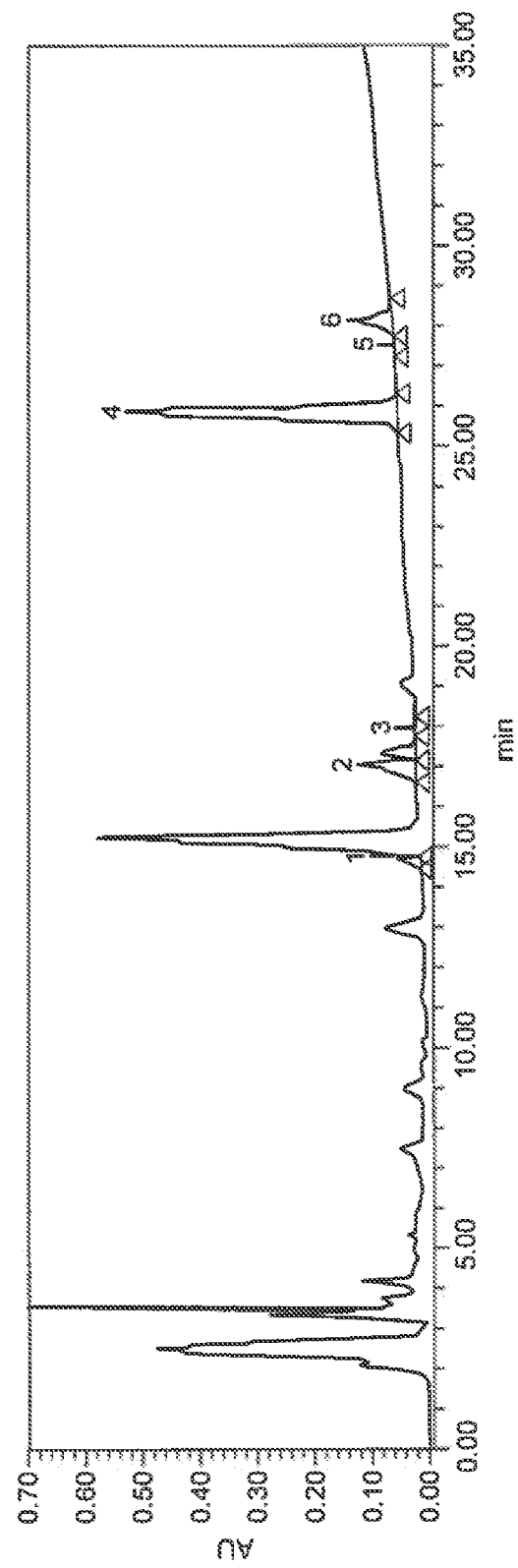
Figure 2C:
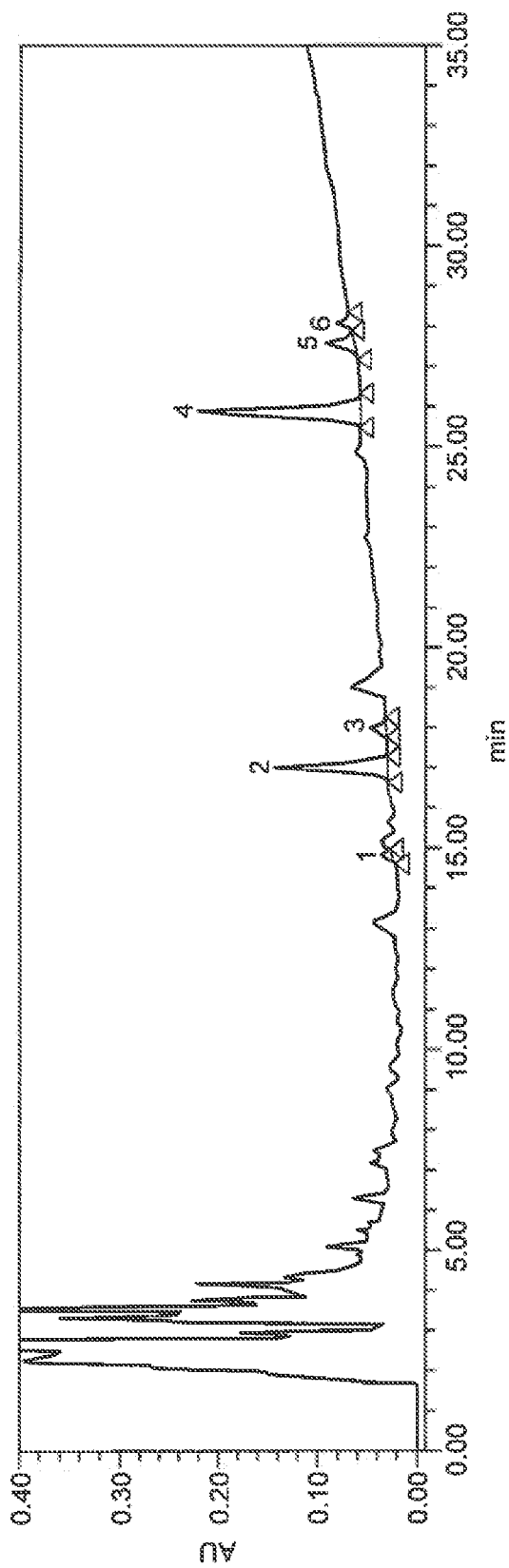
Figure 2D:
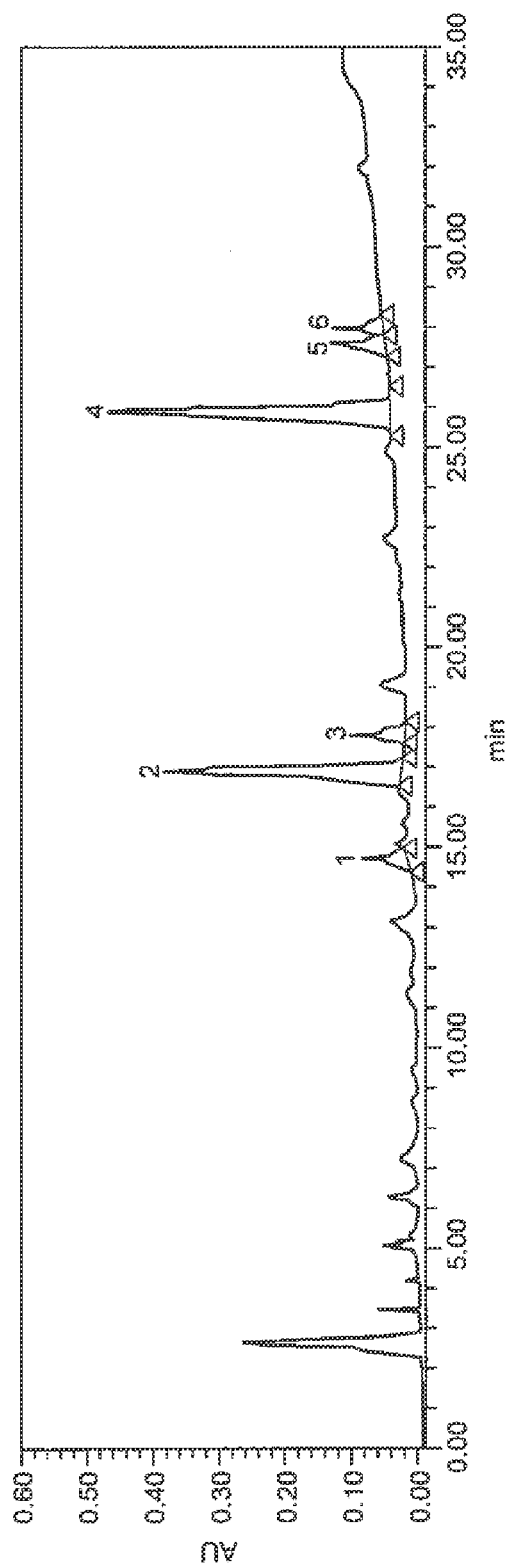
Figure 2E:
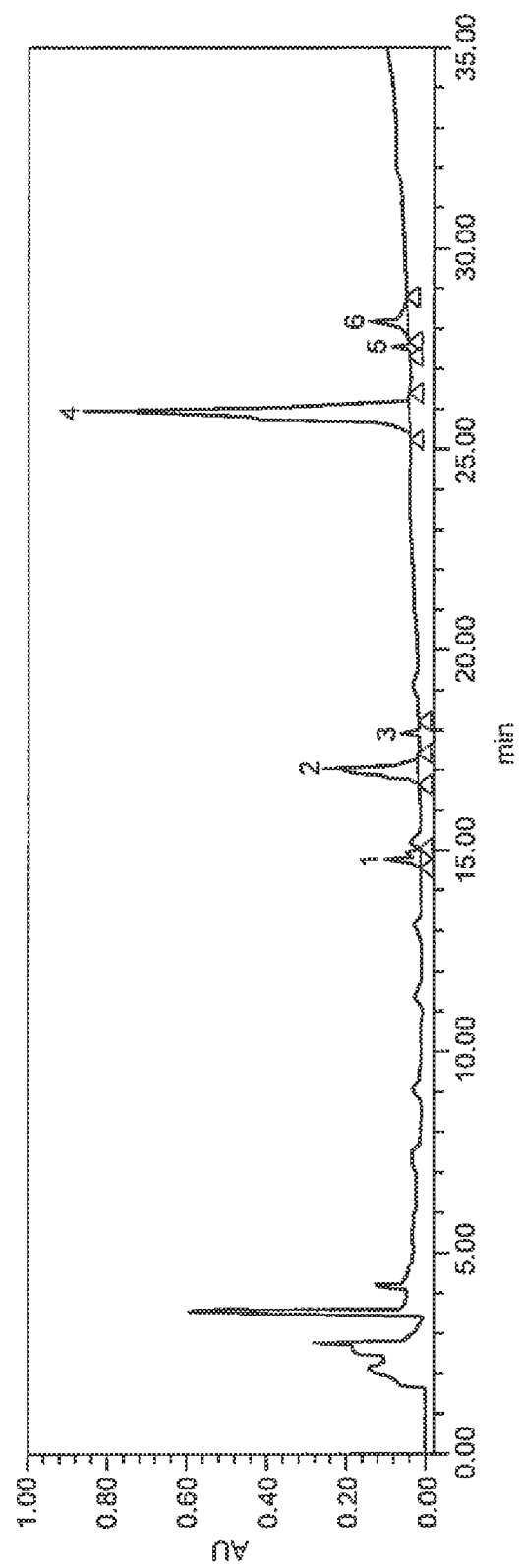
Figure 3:
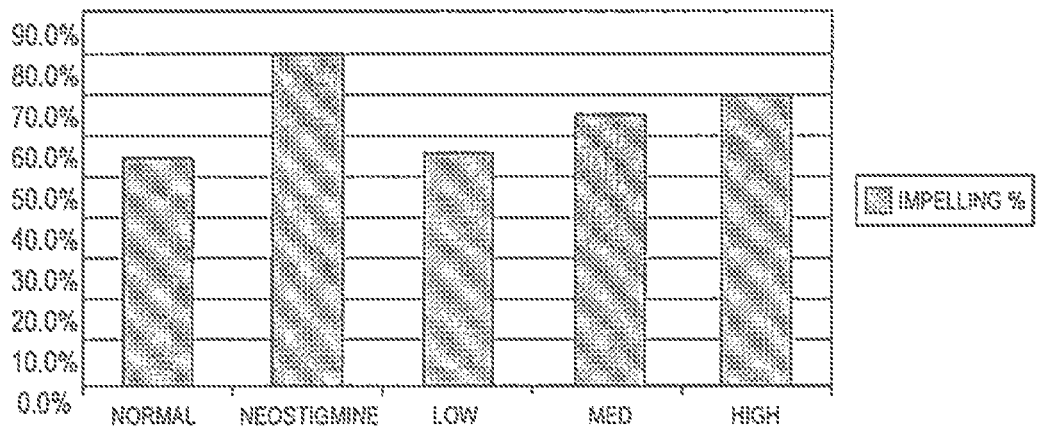
Figure 4:
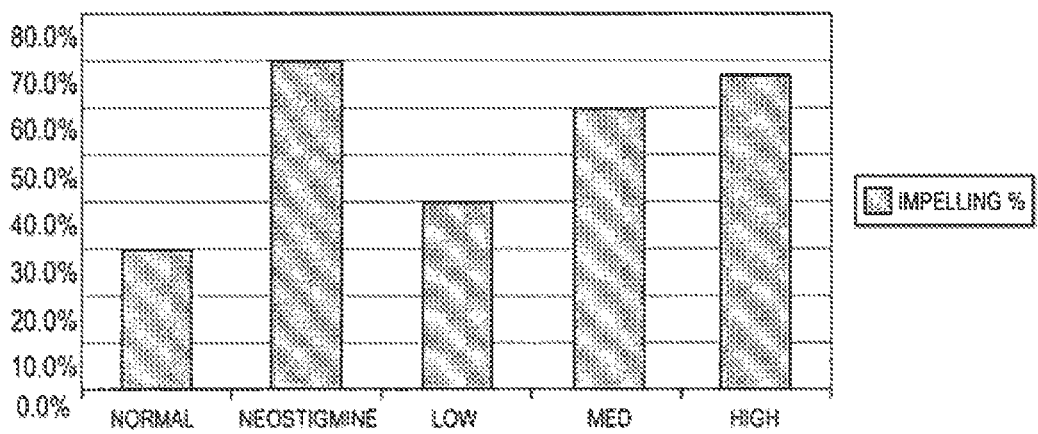
Figure 5:
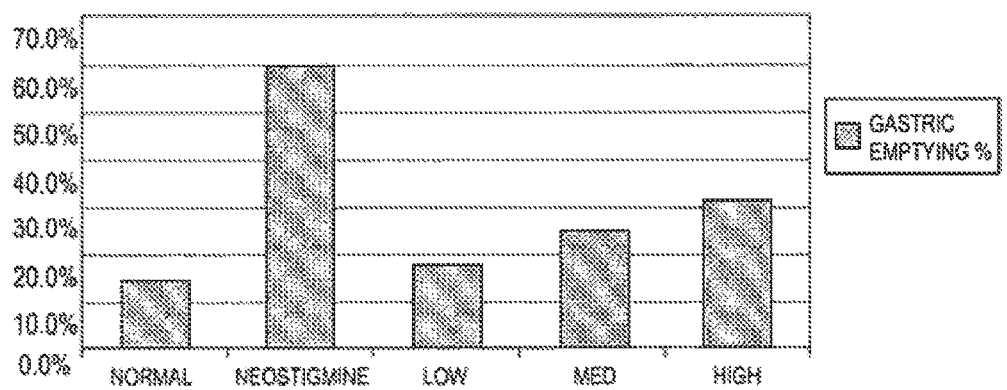
Figure 6:
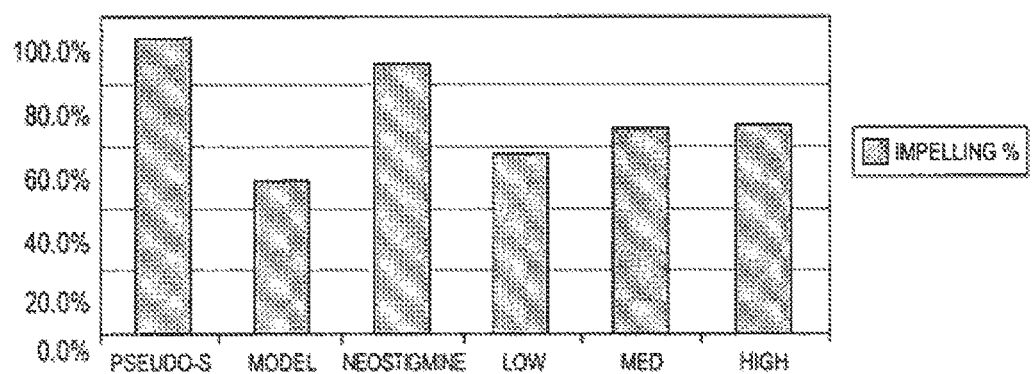
Figure 7:
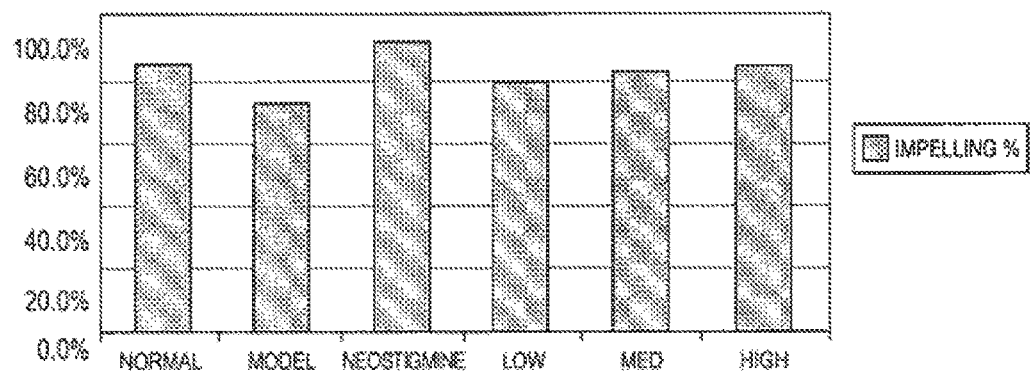
Figure 8:
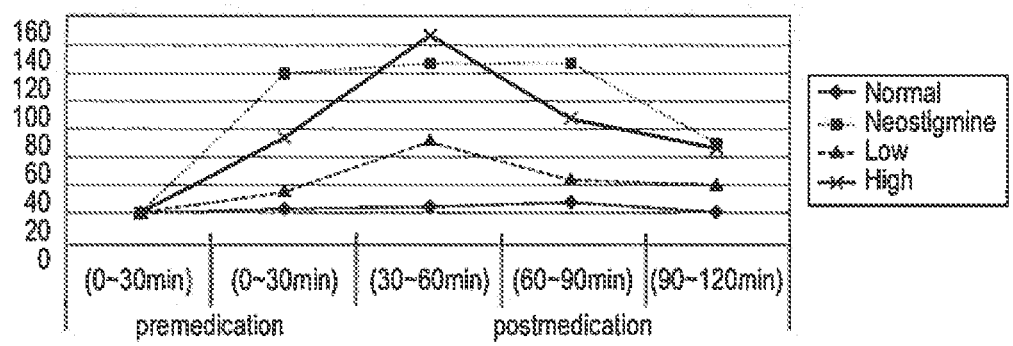
Figure 9:
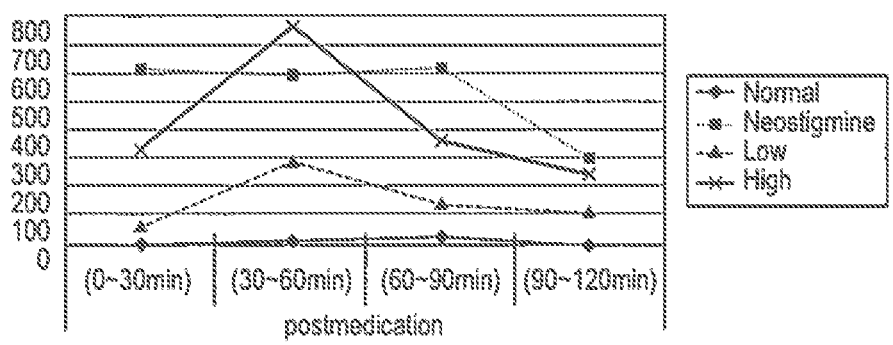
Figure 10:
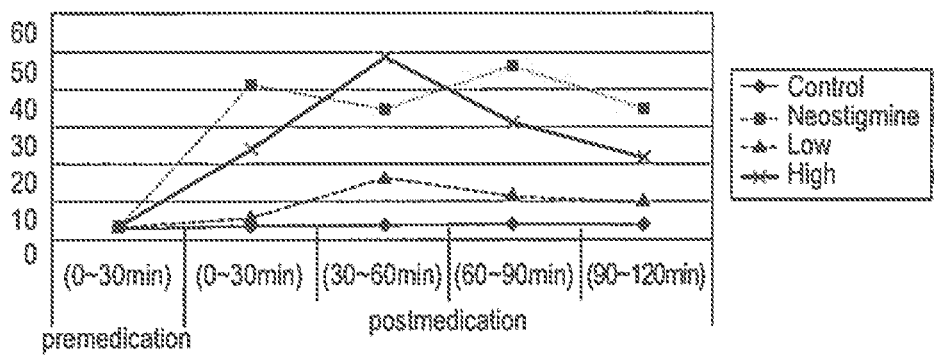
Figure 11:
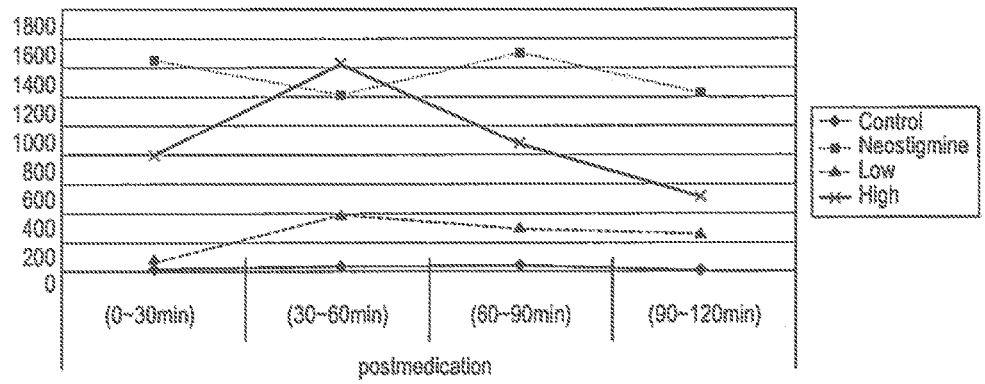
Figure 12:
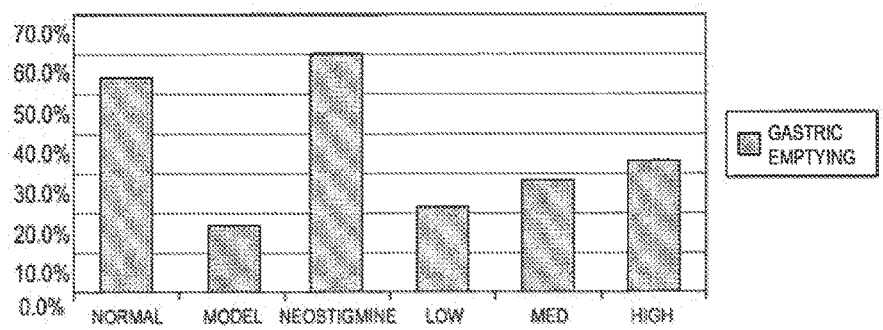
Figure 13:
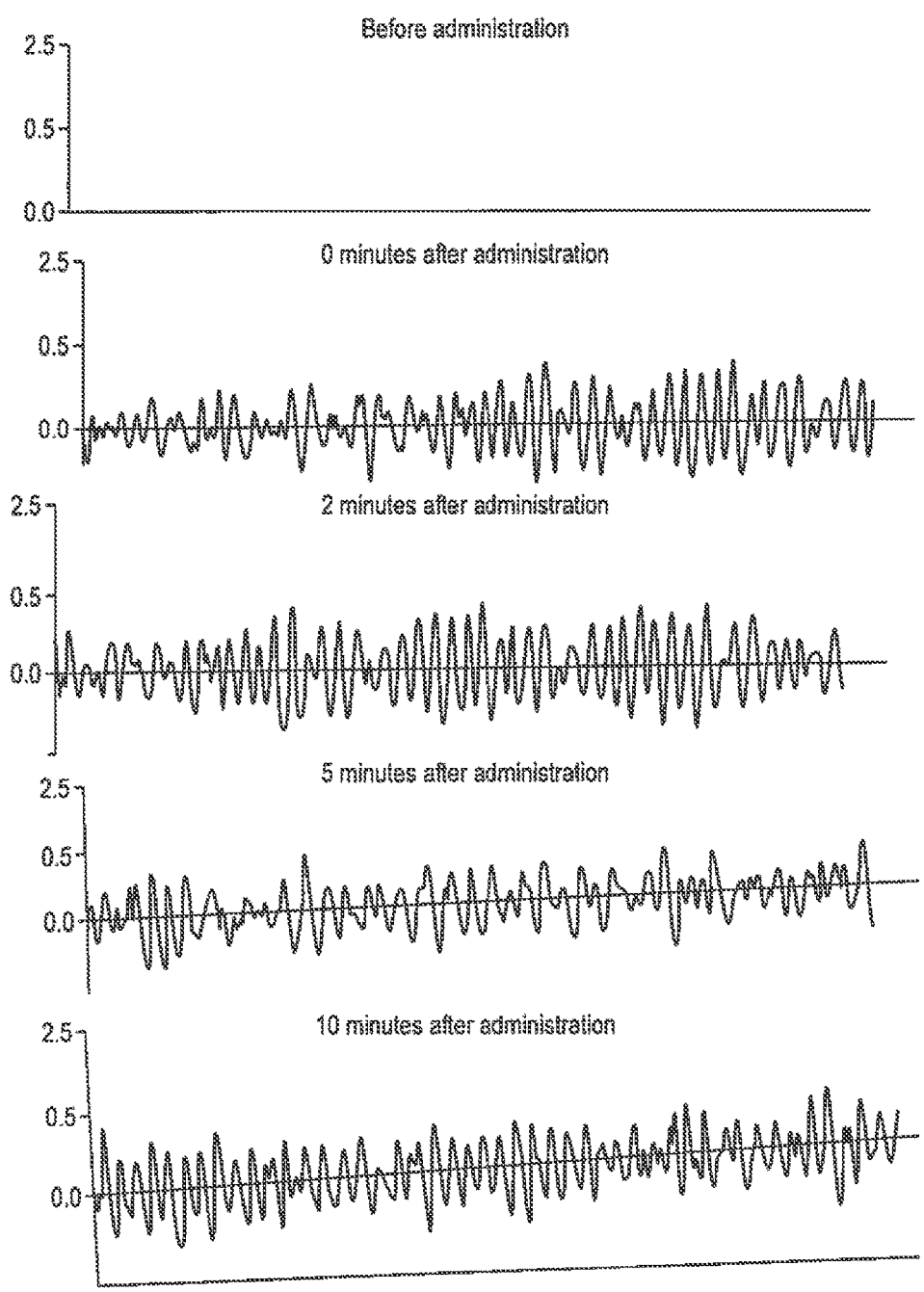

The present invention will be further described, by way of Example only, with reference to the following formulation and data in which:

FIG. 1a shows the chemical structure of Cucurbitacin D;
FIG. 1b shows the chemical structure of Cucurbitacin B;
FIG. 1c shows the chemical structure of Cucurbitacin E;
FIG. 1d shows the chemical structure of Isocucurbitacin B;
FIG. 1e shows the chemical structure of Cucurbitacin A;
FIG. 1f shows the chemical structure of Isocucurbitacin D;
FIG. 2a is an HPLC fingerprint of the first concentrate used in Example 1;
FIG. 2b is an HPLC fingerprint of the Muskmelon Base extract used in Example 2;
FIG. 2c is an HPLC fingerprint of the second concentrate used in Example 1;
FIG. 2d is an HPLC fingerprint of the chloroform purified aqueous extract used in Example 8;
FIG. 2e is an HPLC fingerprint of the extract treated by macro-porous resin as used in Example 11;
FIG. 3 is a graph showing the impelling percentage of the small intestine in normal mice;
FIG. 4 is a graph showing the impelling percentage of large intestine in normal rats;
FIG. 5 is a graph showing the gastric emptying percentage in normal mice;
FIG. 6 is a graph showing the intestinal impelling percentage in mice with mechanical injury;
FIG. 7 is a graph showing the Intestinal impelling percentage in mice with gastrointestinal hypodynamia caused by atropine;
FIG. 8 is a graph showing the number of contractions—effect on proximal colon contraction in anesthetized rats;
FIG. 9 is a graph showing the rate of contractions—effect on proximal colon contraction in anesthetized rats;
FIG. 10 is a graph showing the amplitude indices—effect on proximal colon contraction in anesthetized rats;
FIG. 11 is a graph showing the rate of amplitude—effect on proximal colon contraction in anesthetized rats;
FIG. 12 is a graph showing the gastro emptying test—gastrointestinal hypodynamia in a mouse model caused by atropine; and
FIG. 13 is a graph showing the recorded ex vivo study result—effect of 60 mg/20 ml dose on isolated guinea pig ileum (From the top to the bottom, the recorded waves are: before administration, 0, 2, 5, and 10 minutes after administration).

In each of the HPLC fingerprints (FIGS. 2a-2e):
Peak 1 is Cucurbitacin A;
Peak 2 is Cucurbitacin D;
Peak 3 is Isocucurbitacin D;
Peak 4 is Cucurbitacin B;
Peak 5 is Cucurbitacin E; and
Peak 6 is Isocucurbitacin B.

The chromatographic conditions were as follows:
Column: DIKMA Diamonsil HPLC Column C18 250 mm×4.6 mm, 5 µm
Column Temperature: 30° C.
Wavelength: 232 nm
Flow Rate: 1.0 min/ml
Mobile Phase: A: acetonitrile: tetrahydrofuran (1:1);
B: gradient elution with two-phase of 0.1% phosphoric acid—water (0 min: 30% A; 40 min: 70% A)

DETAILED DESCRIPTION

The detailed description given below is set out in three parts.
   Examples 1 to 13 describe different methods of preparing extracts (extraction and purification) containing Cucurbitacins and the resulting extracts;
   Examples 14 to 18 describe formulations made from a number of these extracts; and
   Experiments 1 to 12 provide details of the studies conducted which provide credible support for the medical indications claimed.

Part 1 Extracts and Extraction/Purification Methodology

The following examples illustrate a variety of methodologies that can be used to obtain Cucurbitacin containing extracts for use in medicine.

EXAMPLE 1

Aqueous Extraction and Ethanolic Precipitation

The raw material of Muskmelon Base (5 kg) was pulverised into a coarse powder and subjected to the following regime:
1. Add 50 kg of water to the coarse powder and boil for approximately 2 hours;
2. Decant the solution;
3. Add a further 40 kg of water to the residue and boil for a further 1 hour, then decant the solution;
4. Add a further 40 kg of water to the residue and boil for a further 1 hour, then decant the solution;
5. Collect the three solutions and filter;
6. Concentrate the solution to obtain a first concentrate (7.5 kg);

7. Add ethanol to the concentrate to get a 70% ethanol solution. Agitate fully, set aside, allow to precipitate for 24 hours and filter;
8. Recover the ethanol to obtain a second concentrate;
9. Spray-dry the second concentrate to obtain a solid extract.

The solid extract obtained had a composition as shown in Table 3 below:

TABLE 3

| Cucurbitacin content | % (by wt of extract) |
|---|---|
| Cucurbitacin B | 0.99 |
| Cucurbitacin D | 0.61 |
| Cucurbitacin E | 0.14 |
| Cucurbitacin A | 0.12 |
| Isocucurbitacin D | 0.09 |
| Isocucurbitacin B | 0.06 |
| TOTAL | |
| Ratio of Cucurbitacin B to Cucurbitacin D | 1.62:1.0 |
| Ratio of Cucurbitacin D to Total Cucurbitacins (including isocucurbitacins) | 0.30:1.0 |

EXAMPLE 2

Solvent Extraction Using Methanol

The raw material of Muskmelon Base (5 kg) was pulverised into a coarse powder and subjected to the following regime:
1. Add 25 kg of methanol and reflux extract with a Soxhlet for 6 hours;
2. Concentrate the liquid extract under vacuum and spray dry to obtain a solid extract.

The solid extract obtained had a composition as shown in Table 4 below:

TABLE 4

| Cucurbitacin content | % (by wt of extract) |
|---|---|
| Cucurbitacin B | 5.83 |
| Cucurbitacin D | 0.63 |
| Cucurbitacin E | 0.03 |
| Cucurbitacin A | 0.36 |
| Isocucurbitacin D | Not detected (<0.01%) |
| Isocucurbitacin B | 0.76 |
| TOTAL | |
| Ratio of Cucurbitacin B to Cucurbitacin D | 9.25:1.0 |
| Ratio of Cucurbitacin D to Total Cucurbitacins (including isocucurbitacins) | 0.08:1.0 |

EXAMPLE 3

Aqueous Extraction and Ethanolic Precipitation (2)

The raw material Muskmelon Base (5 kg) was pulverised into a coarse powder and subjected to the following regime:
1. Add 30 kg of water and boil for 30 minutes,
2. Pour off the solution,
3. Repeat step 1 a further three times,
4. Pool the solutions and filter,
5. Concentrate the solution to obtain a first concentrate (2.5 kg), 6. Add ethanol to form a 65% ethanol solution, agitate fully and set aside to precipitate for 18 hours,
7. Filter, and recover the ethanol under vacuum to obtain a second concentrate,
8. Dry the concentrate under vacuum to obtain a solid extract.

The solid extract obtained had a composition as shown in Table 5 below:

TABLE 5

| Cucurbitacin content | % (by wt of extract) |
|---|---|
| Cucurbitacin B | 0.87 |
| Cucurbitacin D | 0.51 |
| Cucurbitacin E | 0.11 |
| Cucurbitacin A | 0.10 |
| Isocucurbitacin D | 0.07 |
| Isocucurbitacin B | 0.05. |
| TOTAL | |
| Ratio of Cucurbitacin B to Cucurbitacin D | 1.71:1.0 |
| Ratio of Cucurbitacin D to Total Cucurbitacins (including isocucurbitacins) | 0.30:1.0 |

EXAMPLE 4

Ethanolic Extraction

The raw material of Muskmelon Base (4 kg) was pulverised into a coarse powder and subjected to the following regime:
1. Add 25 kg of 75% ethanol and subject it to reflux extraction, with heat, for 4 hours to obtain a liquid extract;
2. Spray-dry the extract to obtain the solid extract.

The solid extract obtained had a composition as shown in Table 6 below:

TABLE 6

| Cucurbitacin content | % (by wt of extract) |
|---|---|
| Cucurbitacin B | 2.91 |
| Cucurbitacin D | 0.58 |
| Cucurbitacin E | Not detected (<0.01%) |
| Cucurbitacin A | 0.18. |
| Isocucurbitacin D | Not detected (<0.01%) |
| Isocucurbitacin B | 0.36 |
| TOTAL | |
| Ratio of Cucurbitacin B to Cucurbitacin D | 5.02:1.0 |
| Ratio of Cucurbitacin D to Total Cucurbitacins (including isocucurbitacins) | 0.14:1.0 |

EXAMPLE 5

Aqueous Extraction and Ethanolic Precipitation (3)

The raw material of Muskmelon Base (3 kg) was pulverized into a coarse powder and subjected to the following methodology.
1. Add 30 kg of water and boil for one hour,
2. Pour off the solution,
3. Repeat step 1 and 2 a further two times,
4. Collect the solutions, filter and concentrate to obtain a first concentrate (5 kg), 5. Add ethanol to form a 75% ethanol solution, agitate fully and set aside for precipitation for 30 hours,
6. Filter and recover the ethanol under vacuum to obtain a second concentrate,
7. Dry the concentrate under vacuum to obtain a solid extract.

The solid extract obtained had a composition as shown in Table 7 below:

TABLE 7

| Cucurbitacin content | % (by wt of extract) |
|---|---|
| Cucurbitacin B | 0.81 |
| Cucurbitacin D | 0.48 |
| Cucurbitacin E | 0.10 |
| Cucurbitacin A | 0.10 |
| Isocucurbitacin D | 0.06 |
| Isocucurbitacin B | 0.04 |
| TOTAL | |
| Ratio of Cucurbitacin B to Cucurbitacin D | 1.69:1.0 |
| Ratio of Cucurbitacin D to Total Cucurbitacins (including isocucurbitacins) | 0.30:1.0 |

EXAMPLE 6

Aqueous Extraction and Ethanol Precipitation (4)

The raw material of Muskmelon Base (4.5 kg) was pulverised into a coarse powder and subjected to the following methodology.
1. Add 35 kg water and boil it for one hour,
2. Pour off the solution,
3. Repeat a further 3 times,
4. Pool the solutions, filter and concentrate to obtain a first concentrates (5 kg),
5. Add ethanol to form an 80% ethanol solution, agitate fully and set aside for precipitation for 30 hours,
6. Filter and recover the ethanol under vacuum to obtain a second concentrate,
7. Spray-dry the concentrates to obtain the solid extract.

The solid extract obtained had a composition as shown in Table 8 below:

TABLE 8

| Cucurbitacin content | % (by wt of extract) |
|---|---|
| Cucurbitacin B | 0.62 |
| Cucurbitacin D | 0.58 |
| Cucurbitacin E | 0.12 |
| Cucurbitacin A | 0.10 |
| Isocucurbitacin D | 0.05 |
| Isocucurbitacin B | 0.06 |
| TOTAL | |
| Ratio of Cucurbitacin B to Cucurbitacin D | 1.07:1.0 |
| Ratio of Cucurbitacin D to Total Cucurbitacins (including isocucurbitacins) | 0.38:1.0 |

EXAMPLE 7

Ethanolic Extraction (2)

The raw material Muskmelon Base (5 kg) was pulverised into a coarse powder and subjected to the following methodology:

1. Add an adequate amount of 50% ethanol to cover the powder and soak at room temperature over night,
2. Apply a percolation method using a further 60 kg of 50% ethanol solution,
3. Concentrate the solution under vacuum,
4. Spray dry to obtain a solid extract.

The solid extract obtained had a composition as shown in Table 9 below:

TABLE 9

| Cucurbitacin content | % (by wt of extract) |
|---|---|
| Cucurbitacin B | 2.78 |
| Cucurbitacin D | 0.42 |
| Cucurbitacin E | Not detected (<0.01%) |
| Cucurbitacin A | Not detected (<0.01%) |
| Isocucurbitacin D | Not detected (<0.01%) |
| Isocucurbitacin B | 0.03 |
| TOTAL | |
| Ratio of Cucurbitacin B to Cucurbitacin D | 6.62:1.0 |
| Ratio of Cucurbitacin D to Total Cucurbitacins (including isocucurbitacins) | 0.13:1.0 |

EXAMPLE 8

Chloroform Purification

The first concentrate, as described in Example 1, was subjected to purification with chloroform as follows:
1. Dissolve the first concentrate in chloroform (⅔ in volume),
2. Separate the chloroform solution,
3. Repeat steps 1 and 2 a further two times,
4. Collect the combined chloroform solutions, recovery the chloroform and dry the residue under vacuum to obtain a solid extract.

The solid extract obtained had a composition as shown in Table 10 below:

TABLE 10

| Cucurbitacin content | % (by wt of extract) |
|---|---|
| Cucurbitacin B | 30.68 |
| Cucurbitacin D | 24.95 |
| Cucurbitacin E | 4.24 |
| Cucurbitacin A | 3.50 |
| Isocucurbitacin D | 4.24 |
| Isocucurbitacin B | 3.50 |
| TOTAL | |
| Ratio of Cucurbitacin B to Cucurbitacin D | 1.23:1.0 |
| Ratio of Cucurbitacin D to Total Cucurbitacins (including isocucurbitacins) | 0.35:1.0 |

EXAMPLE 9

Liquid/Liquid Purification

The liquid extract, as described in Example 2, was taken and the methanol recovered under vacuum as described below.
1. Water was added to the extract (same weight as raw materials) to dissolve the residue and then ether added (the same volume as water) to perform liquid-liquid partition, 2. The ether fraction was recovered and step 1 repeated once again,
3. The ether solutions were combined and the ether recovered,
4. The residue was dried under vacuum to obtain a solid extract.

The solid extract obtained had a composition as shown in Table 11 below:

TABLE 11

| Cucurbitacin content | % (by wt of extract) |
|---|---|
| Cucurbitacin B | 65.79 |
| Cucurbitacin D | 8.45 |
| Cucurbitacin E | 0.42 |
| Cucurbitacin A | 5.04 |
| Isocucurbitacin D | 0.35 |
| Isocucurbitacin B | 9.4 |
| TOTAL | |
| Ratio of Cucurbitacin B to Cucurbitacin D | 7.79:1.0 |
| Ratio of Cucurbitacin D to Total Cucurbitacins (including isocucurbitacins | 0.09:1.0 |

EXAMPLE 10

Liquid/Liquid Purification (2)

The second concentrate as described in Example 5 was taken and further purified as follows:
1. The concentrate was dissolved with water (same weight as of raw material),
2. Liquid-liquid partition was performed with ½ volumes of ethyl acetate 5 times,
3. The ethyl acetate solutions were pooled and ethyl acetate recovered,
4. The residue was dried under vacuum to obtain a solid extract.

The solid extract obtained had a composition as shown in Table 12 below:

TABLE 12

| Cucurbitacin content | % (by wt of extract) |
|---|---|
| Cucurbitacin B | 18.94 |
| Cucurbitacin D | 12.50 |
| Cucurbitacin E | 2.53 |
| Cucurbitacin A | 1.98 |
| Isocucurbitacin D | 1.84 |
| Isocucurbitacin B | 2.02 |
| TOTAL | |
| Ratio of Cucurbitacin B to Cucurbitacin D | 1.52:1.0 |
| Ratio of Cucurbitacin D to Total Cucurbitacins (including isocucurbitacins | 0.31:1.0 |

EXAMPLE 11

Resin Purification

The first concentrate as described in Example 1, was diluted with water and placed onto a column filled with a water pre-balanced macro-porous resin D101 and purified as follows.
1. The column was eluted with water and then with 90% ethanol;
2. The ethanol solution was collected and the ethanol recovered under vacuum;
3. The residue was spray-dried to obtain a solid powder.

The solid extract obtained had a composition as shown in Table 13 below:

TABLE 13

| Cucurbitacin content | % (by wt of extract) |
|---|---|
| Cucurbitacin B | 47.52 |
| Cucurbitacin D | 17.60 |
| Cucurbitacin E | 1.72 |
| Cucurbitacin A | 3.01 |
| Isocucurbitacin D | 1.15 |
| Isocucurbitacin B | 3.72 |
| TOTAL | |
| Ratio of Cucurbitacin B to Cucurbitacin D | 2.70:1.0 |
| Ratio of Cucurbitacin D to Total Cucurbitacins (including isocucurbitacins) | 0.24:1.0 |

EXAMPLE 12

Resin Purification (2)

The second concentrate as described in Example 6, was diluted with water and placed onto a column filled with water pre-balanced macro-porous resin AB-8 and purified as follows.
1. Gradient elution was performed with water then 10%, 50% and 90% ethanol, respectively,
2. The water and 10% ethanol solution were thrown and the 50% and 90% ethanol solutions collected,
3. The ethanol was recovered under vacuum to obtain A solid extract.

The solid extract obtained had a composition as shown in Table 13 below:

TABLE 13

| Cucurbitacin content | % (by wt of extract) |
|---|---|
| Cucurbitacin B | 13.55 |
| Cucurbitacin D | 13.42 |
| Cucurbitacin E | 1.10 |
| Cucurbitacin A | 2.97 |
| Isocucurbitacin D | 0.97 |
| Isocucurbitacin B | 0.80 |
| TOTAL | |
| Ratio of Cucurbitacin B to Cucurbitacin D | 1.01:1.0 |
| Ratio of Cucurbitacin D to Total Cucurbitacins (including isocucurbitacins | 0.41:1.0 |

EXAMPLE 13

Resin Purification (3)

The concentrate as described in Example 7 was diluted with water and placed onto a column filled with water pre-balanced macro-porous resin AB-8 and purified as follows.
1. Gradient elution was performed with water then 10%, 50% and 90% ethanol, respectively,
2. The water and 10% ethanol solution were thrown and the 50% and 90% ethanol solutions collected, 3. The ethanol was recovered under vacuum to obtain the solid extract.

The solid extract obtained had a composition as shown in Table 14 below:

TABLE 14

| Cucurbitacin content | % (by wt of extract) |
| --- | --- |
| Cucurbitacin B | 36.88 |
| Cucurbitacin D | 6.25 |
| Cucurbitacin E | |
| Cucurbitacin A | 0.14 |
| Isocucurbitacin D | |
| Isocucurbitacin B | 1.11 |
| TOTAL | |
| Ratio of Cucurbitacin B to Cucurbitacin D | 5.90:1.0 |
| Ratio of Cucurbitacin D to Total Cucurbitacins (including isocucurbitacins) | 0.14:1.0 |

Part 2 Production of Formulated Medicaments from Extracts

EXAMPLE 14

Formulation for Rectal Delivery

A rectal formulation was made as follows:
1. The solid extract as described in Example 5 was ground into a fine powder,
2. An amount of semi-synthetic glycerides suitable to form unit dosage (1.2 g) suppositories containing a desired dose (90 mg of extract) were taken and melted in a water bath at 40° C.,
3. The solution and powder were mixed and stirred thoroughly,
4. The resulting solution was poured into a mould and cooled.

The resulting rectal suppository contained 90 mg extract standardised against either Cucurbitacin D 0.43 mg and/or Cucurbitacin B 0.73 mg The product has a ratio of Cucurbitacin B:Cucurbitacin D of 1.69:1.0

EXAMPLE 15

Formulation for Rectal Delivery (2)

A rectal formulation was made as follows:
1. The solid extract as described in Example 1 was ground into a fine powder,
2. An adequate amount of 50% ethanol and Tween-80 was added and the mix agitated fully,
3. An amount of semi-synthetic glycerides suitable to form unit dosage suppositories (1.5 g) containing a desired dose of extract (60 mg) were taken and melted in a water bath at 40° C.,
4. The solution and powder were mixed and stirred thoroughly,
5. The resulting solution was poured into a mould and cooled.

The resulting rectal suppository contained 60 mg extract standardised against either Cucurbitacin D 0.37 mg and/or Cucurbitacin B 0.59 mg.

The product has a ratio of Cucurbitacin B:Cucurbitacin D of 1.62:1.0

EXAMPLE 16

Formulation for Rectal Delivery (3)

A rectal formulation was made as follows:
1. The solid extract as described in Example 3 was ground into a fine powder,
2. An adequate amount of cocoa butter and poloxamer (Pluronics) were melted in a water bath at 40° C.,
3. The solution was mixed with the powder and stirred thoroughly,
4. The solution was poured into a mould and allowed to cool.

The resulting rectal suppository (1.5 g) contained 20 mg extract standardised against either Cucurbitacin D 0.10 mg and/or Cucurbitacin B 0.17 mg.

The product has a ratio of Cucurbitacin B:Cucurbitacin D of 1.71:1.0

EXAMPLE 17

Formulation for Rectal Delivery (4)

A rectal formulation was made as follows:
1. Take the solid extract as described in Example 8 and grind into a fine powder,
2. Take an adequate amount of semi-synthetic glycerides and poloxamer (Pluronics) and melt them in a water bath at 40° C.,
3. Mix the solution with the powder and stir thoroughly,
4. Pour the solution into a mould and cool it down.

The resulting rectal suppository (1.2 g) contained 15 mg extract standardised against either Cucurbitacin D 3.74 mg and/or Cucurbitacin B 4.60 mg.

The product has a ratio of Cucurbitacin B:Cucurbitacin D of 1.23:1.0.

EXAMPLE 18

Formulation for Rectal Delivery (5)

A rectal formulation was made as follows:
1. Take the solid extract as described in Example 6 and powder it,
2. Melt an adequate amount of spiceleaf kernal oil (*Lindera communis Hemsl*) and Tween –80 at 40° C. in a water bath,
3. Add the powder into the solution and stir thoroughly,
4. Pour the mixture into the mould and cool it down.

The resulting rectal suppository (1.0 g) contained 50 mg extract standardised against either Cucurbitacin D 0.29 mg and/or Cucurbitacin B 0.31 mg.

The product has a ratio of Cucurbitacin B:Cucurbitacin D of 1.07:1.0

Part 3 Evidence for Claimed Activity

In the following section a solid extract as described in Example 1 was used and for the convenience of understanding, the relationship ratio K of the daily dose per kg body weight between different species is given in the table below.

|   | human | rat | rabbit | mice |
|---|---|---|---|---|
| K | 0.11 | 0.71 | 0.37 | 1 |

EXPERIMENT 1

Maximum Tolerable Dose Test

This experiment was conducted to determine the maximum tolerable dose (MTD), by rectal administration, of an extract of the type described in examples 1.

In this experiment, 10 male and 10 female SD rats weighting 200-240 g were used. They were fasted for 20 hours before the experiment. The rats were given rectal administrations of the Muskmelon-Base extract (diluted with saline to a concentration of 40%) at the dose of 153 mg/kg/d. The reactions of the rats, including behavior, limb movement, intake of water and food, urine and stool were recorded. The investigation lasted for 14 continuous days.

Most of the animals produced watery feces with mucus between 30-120 mins. after medication, and normal feces 6-8 hours after medication. Some animals curled up with little movement at the early stage following medication but returned to normal activity after 30 mins. All the animals grew normally with no death occurring in a 14-day observation period. There was no obvious sign of toxicity and no organ abnormality was found.

The maximum dose of the extract, by rectal administration, was 153 mg /kg/day which is over 200 times the recommended human clinic dose. It indicated that the extract has a good safety profile when administered as a single dose and is a guide for safe clinical use.

EXPERIMENT 2

Rectal Mucosal Irritation Test

The solid extract as described in Example 1 was continuously given to rabbits at both high and low dose for 7 days.

The animals at low dose (4.64 mg/kg) showed no obvious sign of irritation to the rectal mucosa and this dose was equivalent to 7.14 times the recommended human clinical dose of 0.65 mg.

The animals at the high dose (18.55 mg/kg) showed a slight irritation to the rectal mucosa but it was reversible and this dose was equivalent to 28.5 times the recommended human clinical dose of 0.65 mg.

The experimental result suggested that the extract would be non-irritant when administered to humans as a single dose of 0.65 mg/kg/d.

EXPERIMENT 3

Excretion Promotion Study

In this experiment, 50 male ICR mice weighing 23-27 g respectively were divided randomly into 5 groups with 10 per group, i.e. normal control, positive control and three dose groups at 2.48 mg/kg, 4.96 mg/kg and 9.92 mg/kg, respectively. They were fasted for 24 hours before the experiment.

The mice in the positive control group were given an injection of 0.1 ml/10 g body weight of Neostigmine hypodermically while the mice in the normal control groups were given rectal administrations of saline of 0.02 ml/10 g body weight. The mice in the three dose groups were given rectal administrations of the Muskmelon-Base extract (diluted with saline to give desired doses and given 0.02 ml/10 g body weight).

After medication, all the mice were intra-gastrically given infusions of India ink (10% ink, diluted with saline, at the dose 0.02 ml/10 g of body weight). The mice were individually put into a cage with white filter paper flooring. The time of excretion and quantity of the feces were recorded during 4-hour observation periods.

By comparison with the normal control group, and by use of statistical analysis, the duration for the first excretion of black feces of the mice in the positive control group and three dose groups were shortened by 53%, 34%, 39% and 49% (p<0.01), respectively. The quantity of the feces from the positive control group and three dose groups were increased by 49% (p<0.01), 19% (p<0.05), 29% (p<0.01) and 49% (p<0.01), respectively.

The results suggested that the extracts at all three doses could clearly promote excretion in normal mice and the effect was dose dependent.

EXPERIMENT 4

Study on Small Intestine Impelling

In this experiment, 50 male ICR mice weighting 23-27 g respectively were divided randomly into 5 groups with 10 per group, i.e. normal control, positive control and three dose groups at 2.48 mg/kg, 4.96 mg/kg and 9.92 mg/kg, respectively. They were fasted for 24 hours before the experiment. The mice in the positive control group were given an injection of 0.1 ml/10 g body weight of Neostigmine hypodermically while the mice in normal control groups were given rectal administrations of saline of 0.02 ml/10 g body weight. The mice in three dose groups were given rectal administrations of the Muskmelon-Base extract (diluted with saline to desired doses and given 0.02 ml/10 g body weight). Twenty minutes after the medication 10% India ink (diluted with saline) was given to each mouse at the dose of 0.2 ml/10 g body weight.

The mice were killed in 15 minutes and laparotomy was performed. The section of the small intestine from the pylorus to the ileocolic junction was taken out and measured. The impelling percentage was calculated by measuring the whole length of the small intestine and the distance between the pylorus to the front of the ink impelled. (See FIG. 3 for the result).

The two dose groups (intermediate and high dose) clearly showed small intestine impelling effect in the experiment (p<0.01) by comparison with the normal control group.

EXPERIMENT 5

Study on Large Intestine Impelling

This is an efficacy study on the large intestine movement in normal rats after rectal administration of the product.

The experimental result showed that the extract of the invention promotes significant large intestine impelling in rats.

In the experiment, 50 male Wistar rats weighing 200-250 g respectively were divided randomly into 5 groups with 10 per group. They were fasted for 24 hours before the experiment. The rats were etherized in the supine position. A midline incision (1.5-2 cm) was made at the hypogastrium level and the ileocolic junction was taken out delicately using forceps. 10% India ink at 0.2 ml/100 g body weight with Muskmelon-Base extract at the dose of 1.5 mg/kg, 3.0 mg/kg or 6.0 mg/kg was injected into the colon using a syringe. The rats in the normal control and the positive control groups were given injections of saline and 10% ink. The rats in positive control were also given Neostigmine injection (0.08 mg/kg). The incision was sewn up immediately after the injections and a time count was started. The rats were killed and laparotomy was performed 40 minutes after medication. The large intestine from the appendix to the anus was taken out. The total length of the intestine was measured from the start of the colon to the anus. The distance of ink impulsion from the start of the colon to the ink-front was also measured. The impelling percentage was calculated (FIG. 4).

By comparison with the normal control group, the extract at three dose level all exhibited remarkable impelling effect on the large intestine in rats (p<0.01). Some dose-effect relation was observed.

EXPERIMENT 6

Gastric Emptying Experiment

In the experiment, 60 male ICR mice weighting 22-26 g respectively were divided randomly into 5 groups with 12 per group, i.e. normal control, positive control and three dose groups, respectively. They were fasted for 24 hours before the experiment. The mice in the positive control group were given injection of 0.15 ml/10 g body weight of Neostigmine hypodermic while the mice in normal control groups were given rectal administrations of saline. The mice in three dose groups were given rectal administrations of the Muskmelon-Base extract at 2.48 mg/kg, 4.96 mg/kg and 9.92 mg/kg, respectively.

A suspension of 2% carboxymethyl cellulose with 0.05% phenol red was given as gastric infusion to all the mice (0.4 ml/mouse) 30 minutes after medication. The mice were killed and laparotomy was performed in 15 minutes. Both ends of the stomach were tied up and the whole stomach including gastric content was cut into pieces and soaked in 8 ml of 1 mol/L NaOH solution for 2 hours. It was centrifuged at 3000 r/min for 5 minutes. 2.5 ml of the supernatant fluid was taken and 2.5 ml of 10% Trichloroacetic acid was added for albumen precipitation. It was centrifuged again at 3000 r/min for 15 mins. and the supernatant fluid was taken and analyzed with a spectrophotometer at 546 nm.

The percentage of gastric emptying was calculated using the following formula and the results were compared with that of the normal control group.

Percentage of the gastric emptying $(Se)=100-Ps*Pa-1*100$

Ps=phenol red concentration in the mouse stomach (ug/ml)
Pa=phenol red concentration after adding the same volume of 1 mol/L NaOH and Trichloroacetic acid (ug/ml) into the original extract solution By comparison with the normal control group (as shown in FIG. 5), the high-dose group (p<0.01) and the intermediate-dose group (p<0.05) showed a gastric emptying promoting effect with certain dose dependent features.

EXPERIMENT 7

Study on Intestine Enterokinesia in Mice with Mechanical Injury

In this experiment, 72 male ICR mice weighing 22-26 g each were divided randomly into 6 groups with 12 per group. They were named as the pseudo-operation group, the model group, the positive control group (using Neostigmine) and 3 dose groups (low, intermediate and high dose). The mice were fasted for 24 hours before the experiment. The mice in the pseudo-operation group were etherized and a hole was made on each of their abdomens which were sewn up immediately after the incision. The mice in the other groups were also etherized and a hole made in each of their abdomen. Then a half-curved blunt object was inserted into the hole and rotated 5 turns in the anti-clockwise direction to make a simulative mechanical injury and then the hole was sewn up. After the surgery, rectal administrations of saline (0.02 ml/10 g bodyweight) were given to the pseudo-operation group and the model group, and Neostigmine injections (0.15 mg/kg) was given to the positive control group at the dose 0.1 ml/10 g of body weight. The 3 dose groups were given different doses of the Muskmelon-Base extract at the doses of 2.48 mg/kg, 4.96 mg/kg, and 9.92 mg/kg (diluted with saline), respectively.

After medication, intragastric administration of 10% ink was given to the mice at the dose of 0.2 ml/10 g body weight. The mice were killed and laparotomy was performed in 140 minutes. The intestine from the pylorus to the anus was taken out to calculate the impelling percentage by measuring the whole length of the alimentary tract and the distance from the pylorus to the front of the ink impelled (see FIG. 6).

As shown in FIG. 6, the extract in the three dose groups could significantly promote intestine enterokinesia in mice with mechanical injury caused by surgery (p<0.01), which indicated that the extract could significantly promote the recovery of enterokinesia in testing mice.

EXPERIMENT 8

Study on the Intestine Enterokinesia in Mice with Gastrointestinal Hypo-Function Induced by Atropine In this experiment, 66 male ICR mice weighing 22-26 g respectively were divided randomly into 6 groups with 11 per group. They were fasted for 24 hours before the experiment. The 6 groups were named as:
Normal control group,
Model group,
Positive control group, and
The three dose groups.
The mice in the normal control group were only injected saline at 0.1 ml/10 g and mice in all other groups were injected 0.25 mg/kg of Atropine hypodermic at 0.1 ml/10 g body weight.

Twenty minutes after injection Muskmelon-Base extract (diluted with the saline) was given to the mice at the doses of 2.48, 4.96 and 9.96 mg/kg by rectal administration and saline solution was given to the mice in normal, control and the model groups. Neostigmine hypodermic injection (0.15 mg/kg) was given to the mice in the positive control group at the dose 0.1 ml/10 g body weight. A further 20 minutes later, an intragastric administration of 10% ink was given to all the mice at the dose 0.2 ml/10 g body weight.

All the mice were killed and laparotomized in 90 minutes. The intestine from the pylorus to the anus was taken out to measure the whole length of the alimentary tract. The distance from the pylorus to the front the ink impelled was measured to calculate the impelling percentage.

As shown in FIG. 7, Muskmelon-Base extract at all three doses could promote intestinal enterokinesia in mice with gastrointestinal hypo-function induced by atropine (p<0.01), which indicated that the extract could promote the recovery of the hypo-functioned animals. The effect in the high dose group was similar to that of Neostigmine but with no obvious muscle spasm side effect which was always found in all mice in the positive control group.

EXPERIMENT 9

Study on Excretion Intervals and the Quantity of Feces

In this experiment, 66 male ICR mice weighing 22-26 g respectively were divided randomly into 6 groups with 11 per group. They were fasted for 24 hours before the experiment.

The 6 groups were named as:
Normal control group,
Model group,
Positive control group, and
The three dose groups.

The mice in the normal control group were only injected saline at 0.1 ml/10 g and mice in all other groups were injected 0.25 mg/kg of Atropine hypodermic at 0.1 ml/10 g body weight.

Twenty minutes after injection Muskmelon-Base extract (diluted with the saline) was given to the mice at the doses of 2.48, 4.96 and 9.96 mg /kg by rectal administration and saline solution was given to the mice in normal control and the model groups. Neostigmine hypodermic injection (0.15 mg/kg) was given to the mice in positive control group at the dose 0.1 ml/10 g body weight.

A further 20 minutes later, an intragastric administration of 10% ink was given to all the mice at the dose 0.2 ml/10 g body weight. Each mouse was then individually caged in a box with white filter paper on floor. The quantity of the feces and the time of excretion were recorded during 4-hour observation periods.

Compared with the model group, the extract with total Cucurbitacins at the low-dose (p<0.05), intermediate-dose (p<0.01) and high-dose (p<0.01) all significantly shortened excretion intervals in mice with gastrointestinal hypo-function and also increased the quantity of the mice's feces (within 4 hour period). It showed that the extract can activate the intestine enterokinesia restoration in mice with gastrointestinal hypo-function induced by atropine.

EXPERIMENT 10

Study on Proximal Colon Constriction in Anesthetized Rats

In the experiment, 30 male Wistar rats weighing 300-350 g respectively were fasted for 24 hours before the experiment. The rats were anesthetized with 10% Ethyl Carbamate in the supine position on a heat-insulating operating table. The hair on the middle abdomen was cut off and a midline incision (5-6 cm) at the hypogastrium level was made. The colon and ileocolic junction was lifted out delicately using forceps and a colon segment of about 2 cm from the ileocolic junction was selected. Both ends of the segment (the ipsilateral colon tract) were connected by a suture to a fixed tube sheet. Another longer suture was used, with one end connected to the colon wall, while the other end, through the tube, was connected to a JZ100 Muscle Tension Transducer (load 2.0 g). The colon segment was put back into the abdominal cavity, and the incision was sutured with the tube sticking out of the abdominal wall to prevent the colon segment from slipping. A piece of gauze saturated with 0.9% sodium chloride solution was covered on the incision. After surgery, the RM6240 electrophysiology system was connected to record an enterogram.

After the enterokinesia was back to normal an enterogram was started recording. The rectal administration of Muskmelon-base extract was given at the dose of 3.05 mg/kg and 6.10 mg/kg, respectively and the enterogram was recorded for further 2 hours. The following were calculated:

The number of contraction waves in every 30 minutes (FIG. 8).

Amplitude index in every 30 minutes, i.e. total amplitude of all the contraction waves in 30 minutes (FIG. 10).

The percentage of the change of the contraction wave (100% set as before medication). It is calculated as follows: the number of contraction waves in 30 mins. after medication–the number of contraction waves in 30 mins. before medication/the number of contraction waves in 30 mins. before medication×100% (FIG. 9).

The percentage rate of the change of amplitude indices (100% set as before medication). It is calculated as follows: amplitude index in 30 mins. after medication–amplitude index in 30 mins. before medication)/amplitude index in 30 mins. before medication×100%. (FIG. 11).

From the resulting data (FIGS. 8-11), Muskmelon-Base extract at both low and high doses could:
Increase proximal colon movement in anesthetized rats.
It significantly increased
Contraction waves,
The amplitude indices,
The percentage of contraction numbers, and
The percentage of the amplitude index within 30 minutes.
The effect reached a peak between 30 minutes and 60 minutes. A dose-effect relation was also observed.

EXPERIMENT 11

Study on Gastric Emptying

In this experiment, 60 male ICR mice weighing 22-26 g respectively were divided into 6 groups with 10 per group. They were fasted for 24 hours before the experiment.

The 6 groups included:
A normal control group,
A model group,
A positive control group (using Neostigmine), and
Three dose groups.

The mice in the normal, control group were given saline injections whilst the mice in the other 5 groups were given 0.3 mg/kg of atropine hypodermic injections.

The rectal administrations of saline were given to the normal control and the model group. The Muskmelon-Base extract (diluted with saline) was given to the mice in dose groups at 2.48 mg, 4.96 mg and 9.96 mg /kg, respectively.

The mice in positive control were given Neostigmine hypodermic injections (0.15 mg/kg).

Intragastric administration of 0.05% phenol red and 2% carboxymethyl cellulose were given to all the mice at 0.4 ml per mouse 30 minutes after the medication. After 40 minutes the mice were killed and laparotomized. Both ends of the stomach were tied up and the whole stomach including gastric content was cut into pieces and soaked in 8 ml of 1 mol/L NaOH solution for 2 hours. Then it was centrifuged at 3000 r/min for 5 minutes and 2.5 ml of the supernatant fluid was taken. 2.5 ml of 10% Trichloroacetic acid was added for albumen precipitation and the solution was centrifuged again at 3000 r/min for 15 mins. The supernatant fluid was taken and analyzed with a spectrophotometer at 546 nm. The percentage of gastric emptying was calculated by the following formula.

Percentage of the gastric emptying $(Se) = 100 - Ps*Pa-1*100$

Ps=phenol red concentration in the mouse stomach (ug/ml)
Pa=phenol red concentration in the solution of the original extract solution plus the same volume of 1 mol/L NaOH, and Trichloroacetic acid (ug/ml)

As shown in FIG. 12, the extract with total Cucurbitacins at the high dose (9.96 mg/kg) could significantly improve the gastric emptying function of the mice with gastrointestinal hypo-function induced by atropine (P<0.05). The differences in the low and intermediate dose groups showed no significance (P>0.05) compared with the model group although it showed trend towards promotion of gastric emptying effect.

EXPERIMENT 12

Study on Ex Vivo Guinea Pig Ileum (FIG. 13)

In this experiment, healthy, white, non-pregnant female guinea pigs, with a body weight of between 250-350 g were used. The Muskmelon_Base extract was dissolved in 0.9% sodium chloride solution to the required concentrations.

The guinea pigs were sacrificed after 24 hours fasting; the ileum was removed quickly and put into Tyrode's solution saturated with 5% CO2. After a normal cleansing process, it was cut to 1-2 cm and placed in a Magnus bath filled with Tyrode's solution for the measurement of muscle movement using a RM6240 multi-track physiological recorder.

After preparation of isolated ileum, the ileum tension was adjusted to normalize the contraction and the normal movement was recorded using a RM6240 multi-track physiological recorder. 20 ml of test solution was added containing 30 mg, 60 mg and 120 mg extract, respectively and the movement recorded separately. Before the addition of $2^{nd}$ and $3^{rd}$ test solutions, the ileum was washed 2-3 times with 37 degree C. Tyrode's solution to normalize the ileum movement.

As shown in FIG. 13, the extract showed significant effect on increasing the contracting strength of isolated guinea pig ileum.

The invention claimed is:

1. A method for enhancing enterokinesia in a human or animal patient in need thereof comprising the steps of:
   a) administering a standardized extract or pharmaceutical formulation of *Cucumis melo L.* to said patient, the standardized extract comprising Cucurbitacin B and Cucurbitacin D in a weight ratio of from 3:1 to 1:2 and wherein the extract has been standardized against the total weight of all Cucurbitacins in the extract to provide an amount of Cucurbitacin D in the extract based on the total weight of all Cucurbitacins in the extract including Isocucurbitacins of from 8% to 41% by weight, thereby treating or effecting one or more of the following conditions:
   Activating gastroenterokinesia;
   Postoperative gastroenterokinesia restoration;
   Shortening the duration of postoperative flatus;
   Treatment of constipation;
   Treatment of postoperative intestinal adhesion;
   Treatment of Intestinal adhesion and ileus;
   Stimulating gastrointestinal movement in non-surgery;
   Impelling the large and small intestines;
   Activating gastric emptying;
   Smoothing bowel movement; and
   Shortening excretion intervals and increasing the quantity of feces.

2. The method of claim 1 wherein the standardized extract of *Cucumis melo L.* comprises Cucurbitacin D, Cucurbitacin B and at least one of the following:
   Cucurbitacin A, Cucurbitacin E, Isocucurbitacin B and Isocucurbitacin D.

3. The method of claim 1 wherein the standardized extract of *Cucumis melo L.* is a whole extract of Cucurbitacins.

4. The method of claim 1 wherein the standardized extract of *Cucumis melo L.* has a weight ratio of Cucurbitacin B to Cucurbitacin D of from 3:1 to 1:1.

5. The method of claim 1 wherein standardized extract of *Cucumis melo L.* is standardized in its amount of Cucurbitacin B.

6. The method of claim 1 wherein the standardized extract of *Cucumis melo L.* is an aqueous heat reflux extract.

7. The method of claim 6 wherein the standardized extract of *Cucumis melo L.* has an HPLC fingerprint substantially as depicted in FIG. 2a as regards to the compounds Cucurbitacin A peak 1, Cucurbitacin D peak 2, Isocucurbitacin D peak 3, Cucurbitacin B peak 4, Cucurbitacin E peak 5 and Isocucurbitacin B peak 6.

8. The method of claim 1 wherein the standardized extract of *Cucumis melo L.* is an aqueous heat reflux extract which has undergone an alcohol precipitation.

9. The method of claim 8 wherein the standardized extract of *Cucumis melo L.* has a HPLC fingerprint substantially as depicted in FIG. 2c as regards to the compounds Cucurbitacin A peak 1, Cucurbitacin D peak 2, Isocucurbitacin D peak 3, Cucurbitacin B peak 4, Cucurbitacin E peak 5 and Isocucurbitacin B peak 6.

10. The method of claim 1 wherein the standardized extract of *Cucumis melo L.* is a chloroform purified aqueous extract.

11. The method of claim 10 wherein the standardized extract of *Cucumis melo L.* has a an HPLC fingerprint substantially as depicted in FIG. 2d as regards to the compounds Cucurbitacin A peak 1, Cucurbitacin D peak 2, Isocucurbitacin D peak 3, Cucurbitacin B peak 4, Cucurbitacin E peak 5 and Isocucurbitacin B peak 6.

12. The method of claim 1 wherein the standardized extract of *Cucumis melo L.* is an alcoholic extract.

13. The method of claim 12 wherein the standardized extract of *Cucumis melo L.* has a an HPLC fingerprint substantially as depicted in FIG. 2b as regards to the compounds Cucurbitacin A peak 1, Cucurbitacin D peak 2, Isocucurbitacin D peak 3, Cucurbitacin B peak 4, Cucurbitacin E peak 5 and Isocucurbitacin B peak 6.

14. The method of claim 1 wherein the standardized extract of *Cucumis melo L.* has undergone a resin purification step.

15. The method of claim 14 wherein the standardized extract of *Cucumis melo L.* has a an HPLC fingerprint substantially as depicted in FIG. 2e as regards to the compounds Cucurbitacin A peak 1, Cucurbitacin D peak 2, Isocucurbitacin D peak 3, Cucurbitacin B peak 4, Cucurbitacin E peak 5 and Isocucurbitacin B peak 6.

16. The method of claim 1 comprising administering a pharmaceutical formulation comprising the standardized extract of *Cucumis melo L.* in unit dosage form.

17. The method of claim 16 wherein the pharmaceutical formulation comprises Cucurbitacin D in an amount to provide a daily dose containing from 0.0040 mg to 40 mg of Cucurbitacin D.

18. The method of claim 17 wherein the pharmaceutical formulation comprises Cucurbitacin D in an amount to provide a daily dose containing from 0.040 mg to 4 mg of Cucurbitacin D.

19. The method of claim 18 wherein the pharmaceutical formulation comprises Cucurbitacin D in an amount to provide a daily dose containing from 0.1 mg to 1.6 mg of Cucurbitacin D.

20. The method of claim 16 wherein the pharmaceutical formulation comprises Cucurbitacin B in an amount to provide a daily dose containing from 0.0064 mg to 64 mg of Cucurbitacin B.

21. The method of claim 20 wherein the pharmaceutical formulation comprises Cucurbitacin B in an amount to provide a daily dose containing from 0.064 mg to 6.4 mg of Cucurbitacin B.

22. The method of claim 21 wherein the pharmaceutical formulation comprises Cucurbitacin B in an amount to provide a daily dose containing from 0.16 mg to 2.6 mg of Cucurbitacin B.

23. The method of claim 16 wherein the pharmaceutical formulation has a weight ratio of Cucurbitacin B:Cucurbitacin D of from 3:1 to 1:1.

24. The method of claim 16 wherein the pharmaceutical formulation is administered by rectal administration.

25. The method of claim 24 wherein the pharmaceutical formulation is a suppository.

26. The method of claim 1 wherein administration of the standardized extract or pharmaceutical formulation does not produce muscle spasm as a side effect.

* * * * *